United States Patent
Fujigasaki et al.

(10) Patent No.: US 11,567,310 B2
(45) Date of Patent: Jan. 31, 2023

(54) SWITCH UNIT AND ENDOSCOPE

(71) Applicant: OLYMPUS CORPORATION, Tokyo (JP)

(72) Inventors: Masatoshi Fujigasaki, Shirakawa (JP); Masanori Yajima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 290 days.

(21) Appl. No.: 15/930,980

(22) Filed: May 13, 2020

(65) Prior Publication Data

US 2020/0268232 A1 Aug. 27, 2020

Related U.S. Application Data

(63) Continuation of application No. PCT/JP2018/031931, filed on Aug. 29, 2018.

(30) Foreign Application Priority Data

Nov. 16, 2017 (JP) .............................. JP2017-220621

(51) Int. Cl.
*H01H 13/14* (2006.01)
*G02B 23/24* (2006.01)
(Continued)

(52) U.S. Cl.
CPC ...... *G02B 23/2476* (2013.01); *A61B 1/00042* (2022.02); *H01H 13/14* (2013.01);
(Continued)

(58) Field of Classification Search
CPC ...... H01H 3/125; H01H 13/705; H01H 13/14; H01H 13/04; H01H 13/10; H01H 13/70;
(Continued)

(56) References Cited

U.S. PATENT DOCUMENTS

| 4,625,723 A * | 12/1986 | Altnether ........... A61B 18/1402 |
| | | 606/49 |
| 2007/0219409 A1 * | 9/2007 | Shimizu ............. H01H 36/0013 |
| | | 600/101 |

(Continued)

FOREIGN PATENT DOCUMENTS

| CN | 104576130 A | 4/2015 |
| JP | S61-167330 U | 10/1986 |

(Continued)

OTHER PUBLICATIONS

International Search Report dated Nov. 27, 2018 issued in PCT/JP2018/031931.

*Primary Examiner* — Ahmed M Saeed
(74) *Attorney, Agent, or Firm* — Scully, Scott, Murphy & Presser, P.C.

(57) ABSTRACT

A switch unit includes: a tactile switch; a cable which transmits an operation signal generated when the tactile switch is operated; a formed part where a fitting engagement portion which is disposed on an operation section exterior member at a predetermined position, a recessed surface which is formed on a side of a first end portion with respect to the fitting engagement portion and where the tactile switch is mounted, a cable fixing portion which is disposed on a side of a second end portion which is a side opposite to the first end portion with the fitting engagement portion positioned between the first end portion and the second end portion and to which the cable is connected, and a circuit which electrically connects the recessed surface and the cable fixing portion to each other and transmits an operation signal generated by the tactile switch to the cable are formed.

13 Claims, 14 Drawing Sheets

(51) Int. Cl.
*H01H 13/52* (2006.01)
*A61B 1/00* (2006.01)
*H04N 5/225* (2006.01)
*H04N 7/18* (2006.01)

(52) U.S. Cl.
CPC ....... *H01H 13/52* (2013.01); *H01H 2300/014* (2013.01); *H04N 5/2253* (2013.01); *H04N 7/183* (2013.01); *H04N 2005/2255* (2013.01)

(58) Field of Classification Search
CPC ............. H01H 13/704; H01H 13/7065; H01H 13/7006; H01H 13/7057; H01H 13/78; H01H 13/79; H01H 13/52; H01H 13/703; H01H 13/507; H01H 3/12; H01H 13/20; H01H 2300/014; H01H 13/81; A61B 1/00039; A61B 1/00042; A61B 1/0052; G02B 23/2476; H04N 5/2253; H04N 7/183; H04N 2005/2255
See application file for complete search history.

(56) References Cited

U.S. PATENT DOCUMENTS

2015/0230693 A1  8/2015  Kubo et al.
2017/0236659 A1  8/2017  Sanai et al.

FOREIGN PATENT DOCUMENTS

| JP | 2002-025387 A | 1/2002 |
| JP | 2007-087012 A | 4/2007 |
| JP | 2007-252418 A | 10/2007 |
| JP | 2011-243300 A | 12/2011 |
| WO | WO 2014/171275 A1 | 10/2014 |
| WO | WO 2016/098664 A1 | 6/2016 |

* cited by examiner

SWITCH UNIT AND ENDOSCOPE

CROSS REFERENCE TO RELATED APPLICATION

This application is a continuation application of PCT/JP2018/031931 filed on Aug. 29, 2018 and claims benefit of Japanese Application No. 2017-220621 filed in Japan on Nov. 16, 2017, the entire contents of which are incorporated herein by this reference.

BACKGROUND OF THE INVENTION

1. Field of the Invention

The present invention relates to a switch unit provided to an endoscope operation section, and an endoscope where an operation switch having the switch unit is mounted on the operation section.

2. Description of the Related Art

Endoscopes have been used in the medical field, the industrial field and the like. Endoscopes include an elongated insertion section inserted into a subject. In general, an image pickup apparatus is incorporated in a distal end portion positioned on a distal end side of the insertion section. A bending portion is mounted on the distal end side of the insertion section such that the bending portion is connected to the distal end portion.

On the other hand, an endoscope operation section (hereinafter, referred to as an operation section) is mounted on a proximal end side of the insertion section. An operation lever which tows or slackens a bending wire by a hand-side operation of a user, an operation switch for instructing stopping of an endoscope image, recording of the image, switching of illumination light and the like, and operation buttons such as a water feeding button and a suction button are mounted on the operation section.

In the medical field, endoscopes are used in a respiratory department, an otolaryngology department, a urology department, and other diagnosis and treatment departments. Conventionally, to realize the reduction of a cost of an endoscope, for example, operation sections have basically adopted the common basic structure with respect to an overall shape of the operation section, the structure and the arrangement position of an operation lever, the structure and the arrangement position of an operation switch and the like.

As shown in FIG. 1A, an exterior member of an endoscope operation section (hereinafter, abbreviated as an operation section exterior) 1 includes, for example, two remote switches 2 as operation switches. The remote switch 2 mainly has a key top 3, a guide tube 4, a guide tube fixing member 5, a switch unit 6, and a unit fixing member 7. The switch unit 6 is disposed in an operation section inner space 1S.

As shown in FIG. 1B, stepped holes 1h which communicate with the outside of an operation section and the operation section inner space 1S are formed in the operation section exterior 1. The stepped hole 1h has a small diameter hole 1a and a large diameter hole 1b. An opening of the large diameter hole 1b forms an outside opening. Symbol 1d indicates a bottom surface of the large diameter hole 1b. An opening of the small diameter hole 1a forms a bottom surface opening and a space-side opening.

With reference to FIG. 1C, the description is made with respect to the key top 3, the guide tube 4, the guide tube fixing member 5, the switch unit 6, and the switch fixing member 7 which form the remote switch 2.

The key top 3 is an elastic rubber member and is formed in a predetermined shape. The key top 3 mainly has a finger touch portion 3a and a shaft portion 3b. Symbol 3c is an inner flange portion, and protrudes toward an inner space side of the finger touch portion 3a. The finger touch portion 3a functions as both a button portion and a cover member.

The finger touch portion 3a is accommodated in the large diameter hole 1b as shown in FIG. 1A. An outer peripheral surface 3d is disposed in a close contact manner with an inner peripheral surface of the large diameter hole 1b. A lower end surface 3e of the inner flange portion 3c is disposed on a bottom surface 1d of the large diameter hole 1b.

The shaft portion 3b shown in FIG. 1C protrudes from a center of the finger touch portion 3a. A length of the shaft portion 3b is set in advance such that an end surface of the shaft portion 3b is disposed in the operation section inner space 1S.

The guide tube 4 has an outer flange portion 4a, a pipe portion 4b, and a shaft portion hole 4c which is an axial through hole. The outer flange portion 4a is disposed in a space in the finger touch portion 3a, and is placed on the inner flange portion 3c. The pipe portion 4b protrudes from one end surface of the outer flange portion 4a, and has a length set in advance. A male threaded portion 4m is formed on an intermediate portion of the pipe portion 4b.

Note that one end surface of the pipe portion 4b is disposed in the operation section inner space 1S. In this embodiment, a length of the pipe portion 4b is set such that the shaft portion 3b of the key top 3 protrudes from an end surface of the pipe portion 4b.

The guide tube fixing member 5 has, for example, a first outer flange portion 5a, a second outer flange portion 5b, an escape peripheral groove 5c, and a stepped hole 5d. The stepped hole 5d is an axial through hole, and has an escape hole 5e, a threaded hole 5f, and a fitting engagement hole 5g. The shaft portion 3b is fitted in the fitting engagement hole 5g. Female threads are formed on an inner peripheral surface of the threaded hole 5f. The female threads of the threaded hole 5f threadedly engage with the male threaded portion 4m of the pipe portion 4b.

A pair of mounting holes 5h is formed in the second outer flange portion 5b in which the fitting engagement hole 5g is formed. The mounting holes 5h are axial through holes in which projections of a so-called pin face wrench which forms a mounting tool are disposed.

An end surface 5i of the first outer flange portion 5a forms a mounting surface, and the end surface 5i is disposed on one surface side of a fixing plate described later (indicated by symbol 8 in FIG. 1A).

The switch unit 6 includes: one circuit board 6a on which a circuit is formed; two tactile switches 6b, and electric cables 6c which are connected to the respective tactile switches 6b. Switch contacts (not shown in the drawing) and cable contacts (not shown in the drawing) are disposed in the circuit of the circuit board 6a. The tactile switch 6b is mounted on the switch contact. One end portion of the electric cable 6c is connected to the cable contact. Symbol 6h indicates an axial through hole 6h which is formed in the circuit board 6a.

The unit fixing member 7 includes a fixing portion body 7A, a nut 7B, and a screw member 7C. The fixing portion body 7A has an outer flange portion 7d, one end side shaft portion 7e, and the other end side shaft portion 7g, and an axial through hole 7h.

One end side shaft portion 7e protrudes from one end surface of the outer flange portion 7d. The other end side shaft portion 7g protrudes from the other end surface which is a surface of the outer flange portion 7d disposed opposite to one end surface of the outer flange portion 7d.

A male threaded portion 7m is formed on an end surface side of one end side shaft portion 7e. A female threaded portion 7f of the nut 7B which forms a fixing member threadedly engages with the male threaded portion 7m. A shaft portion 7Ca of the screw member 7C which forms the fixing member passes through the through hole 7h (loose fitting arrangement). The shaft portion 7Ca has a male threaded portion 7Cm. An end portion of the shaft portion 7Ca is inserted into the through hole 7h from one end side opening, and a length of the shaft portion 7Ca is set such that the end portion of the shaft portion 7Ca protrudes to the outside from the other end side opening.

Symbol 8 in FIG. 1A indicates the fixing plate. The fixing plate 8 is fixed by adhesion, for example, to a fixing surface 1f which is a planar surface formed on the operation section exterior 1 at a predetermined position on an operation section inner space 1S side. Guide tube insertion holes 8a and a threaded hole 8b are formed in the fixing plate 8. A shaft portion 9Aa of a mounting screw 9A which forms a fixing member and has a male threaded portion 9Am is inserted into and disposed in the threaded hole 8b.

Symbol 9B in FIG. 1A and FIG. 1C indicates a fixing pipe. A threaded hole 9f (not shown in FIG. 1A) which is a through hole extending along a center axis and has a female threaded portion is formed in the fixing pipe 9B. The fixing pipe 9B is mounted on the fixing plate 8 in advance by the mounting screw 9A.

Mounting of the remote switches 2 on the operation section exterior 1 is described.

An operator prepares the operation section exterior 1, the key tops 3, the guide tube 4, the guide tube fixing members 5, the switch unit 6, and the unit fixing member 7.

In the description made below, mounting of the remote switch 2 in one of stepped holes 1h formed in the operation section exterior 1 is described.

The operator forms a key top set 10 shown in FIG. 2A in advance. The key top set 10 is a member which is formed by integrally assembling the key top 3 and the guide tube 4 to each other. More specifically, the operator inserts the shaft portion 3b of the key top 3 into the shaft hole 4c of the pipe portion 4b of the guide tube 4, and arranges the outer flange portion 4a of the guide tube 4 in the finger touch portion 3a.

Further, the operator forms a switch set 11 shown in FIG. 2B in advance. The switch set 11 is a member which is formed by integrally assembling the switch unit 6, the fixing portion body 7A, and the nut 7B to each other. More specifically, the operator inserts one end side shaft portion 7e of the fixing portion body 7A into the axial through hole 6h of the circuit board 6a on which the tactile switch 6b is mounted and to which the electric cables 6c are connected, and places one surface side of the outer flange portion 7d on the circuit board 6a. Then, the female threaded portion 7f of the nut 7B is threadedly engages with the male threaded portion 7m of one end side shaft portion 7e. As a result, the circuit board 6a is sandwiched and fixed between the outer flange portion 7d and the nut 7B.

The operator first inserts the shaft portion 3b of the key top 3 which forms the key top set 10 into the small diameter hole 1a as shown in FIG. 2C, introduces the pipe portion 4b of the guide tube 4 into the small diameter hole 1a, and arranges the finger touch portion 3a of the key top 3 in the large diameter hole 1b.

As a result, the finger touch portion 3a of the key top 3 is disposed in the large diameter hole 1b, and the pipe portion 4b including the male threaded portion 4m and the shaft portion 3b are arranged in the operation section inner space 1S as shown in FIG. 2D.

Next, the operator first arranges the fixing plate 8 on the fixing surface 1f of the operation section exterior 1 at the predetermined position as shown in FIG. 2D. Note that the fixing pipe 9B is threadedly fixed to the fixing plate 8 using the mounting screw 9A. The guide tube insertion hole 8a is formed in the fixing plate 8, and the pipe portion 4b and the shaft portion 3b are inserted into and arranged in the escape hole 8h.

Next, the operator mounts the guide tube fixing member 5 on the guide tube 4 which forms the key top set 10 and protrudes into the operation section inner space 1S. In other words, the male threaded portion 4m of the pipe portion 4b of the guide tube 4 is threadedly engaged with the threaded hole 5f of the guide tube fixing member 5 having female threads. With such threaded engagement, the shaft portion 3b is further moved into the operation section inner space 1S as indicated by an arrow Y2D.

As a result, as shown in FIG. 2E, the end surface 5i of the guide tube fixing member 5 is brought into contact with one surface of the fixing plate 8 so that the fixing plate 8 is sandwiched and fixed between the end surface 5i and the fixing surface 1f, and the key top set 10 is fixedly mounted on the operation section exterior 1. At this stage of operation, the outer flange portion 4a presses the inner flange portion 3c so that the inner flange portion 3c is elastically deformed, the outer peripheral surface 3d is brought into close contact with an inner peripheral surface of the large diameter hole 1b, and the lower end surface 3e is brought into close contact with the bottom surface 1d.

Next, the operator mounts the switch set 11 on the fixing pipe 9B which is integrally fixed to the operation section exterior 1 as shown in FIG. 2E. In other words, an end surface of the other end side shaft portion 7g of the fixing portion body 7A which forms the switch set 11 is brought into contact with an end surface of the fixing pipe 9B as indicated by a broken line. At this stage of operation, the tactile switch 6b and the shaft portion 3b of the key top 3 are made to face each other in a predetermined state.

Then, the operator integrally mounts the switch set 11 on the fixing pipe 9B which is integrally formed with the operation section exterior 1 by making the shaft portion 7Ca of the screw member 7C threadedly engage with the threaded hole 9f of the pipe 9B through the through hole 7h of the fixing portion body 7A.

With such operations, a state is brought about where the remote switch 2 is mounted on the operation section exterior 1 as shown in FIG. 1.

Japanese Patent Application Laid-Open Publication No. 2007-87012 discloses an input apparatus. In this input apparatus, a second circuit board is mounted in a lower case in a fixed state, and a tactile switch is disposed on an upper surface of the second circuit board. The tactile switch forms a switch element for deciding inputting. A pressing convex portion is formed on a lower surface of an upper cover corresponding to an operating element of a tactile switch. The upper cover is biased upward by a compression coil spring.

In the input apparatus having the above-mentioned configuration, when the upper cover is operated downward by pressing, the operating element is operated by pressing by way of the pressing convex portion, and the tactile switch is turned on in response to such a pressing operation. When a pressing force applied to the upper cover is released, the upper cover is returned upward due to a biasing force of the compression coil spring and hence, pressing of the operating element is released and the tactile switch is returned to an OFF state.

SUMMARY OF THE INVENTION

According to an aspect of the present invention, there is provided a switch unit which is mounted on an exterior member, the switch unit includes: a tactile switch; a cable configured to transmit a signal of the tactile switch; and a formed part disposed on the exterior member at a predetermined position, wherein the formed part includes: a switch fixing portion which is disposed on a side of a first end portion and on which the tactile switch is mounted; a cable fixing portion which is disposed on a side of a second end portion and to which the cable is connected; and a circuit which electrically connects the switch fixing portion and the cable fixing portion.

According to another aspect of the present invention, there is provided an endoscope which includes the switch unit in an endoscope operation section.

According to still another aspect of the present invention, there is provided an endoscope which includes: an insertion section; an operation section which is mounted on a proximal end side of the insertion section; a universal cord which extends sideward from the operation section; a tactile switch which is mounted on the operation section; a cable which is disposed in the universal cord and is configured to transmit a signal of the tactile switch; a formed part which includes an intermediate portion which is disposed on the operation section at a predetermined position, a switch fixing portion which is disposed on a side of a first end portion with respect to the intermediate portion, and on which the tactile switch is mounted, and a cable fixing portion which is disposed on a side of a second end portion which is a side opposite to the first end portion with the intermediate portion positioned between the first end portion and the second end portion, and to which the cable is connected; and a circuit which is disposed on the formed part and electrically connects the switch fixing portion and the cable fixing portion to each other.

DETAILED DESCRIPTION OF THE PREFERRED EMBODIMENTS

Hereinafter, an embodiment of the present invention is described with reference to drawings.

In the respective drawings used in the description made hereinafter, to set sizes of respective constitutional elements to a degree that allows the respective constitutional elements recognizable on the drawings, there may be a case where the magnification is made different for respective constitutional elements. In other words, the present invention is not limited to only the number of constitutional elements, shapes of the constitutional elements, ratios between sizes of the constitutional element, and the relative positional relationship between the respective constitutional elements described in these drawings.

Recently, in an endoscope, an operation section having a shape optimal for each diagnosis and treatment department has been desired.

Figure 1A:
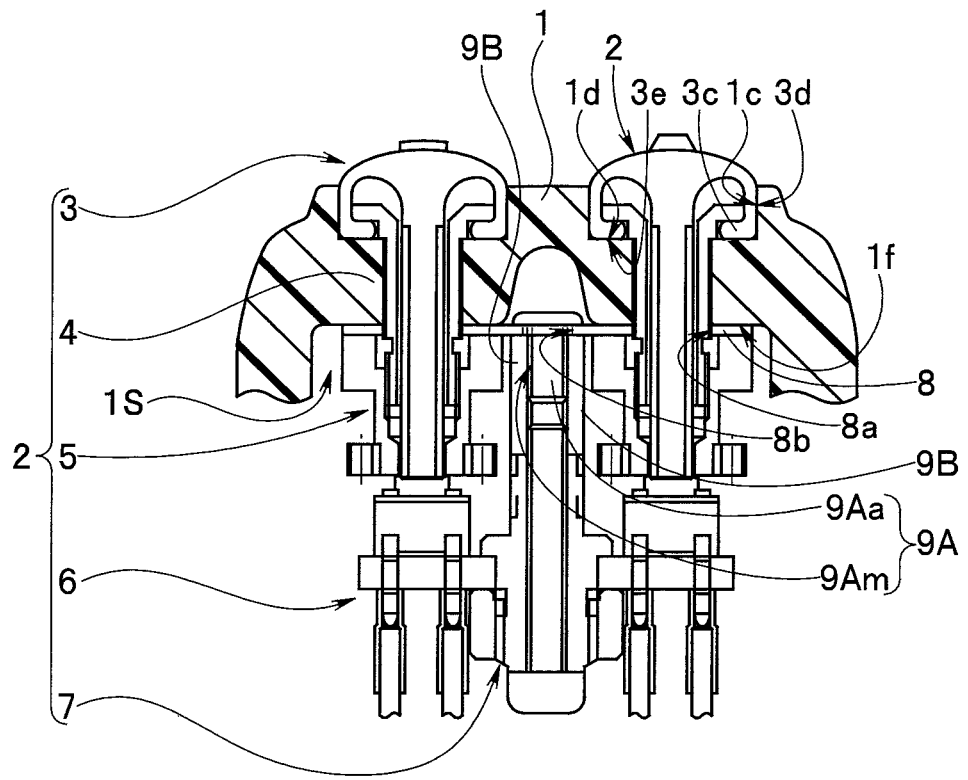
FIG. 1A is a view illustrating an operation section exterior and remote switches.
Figure 1B:
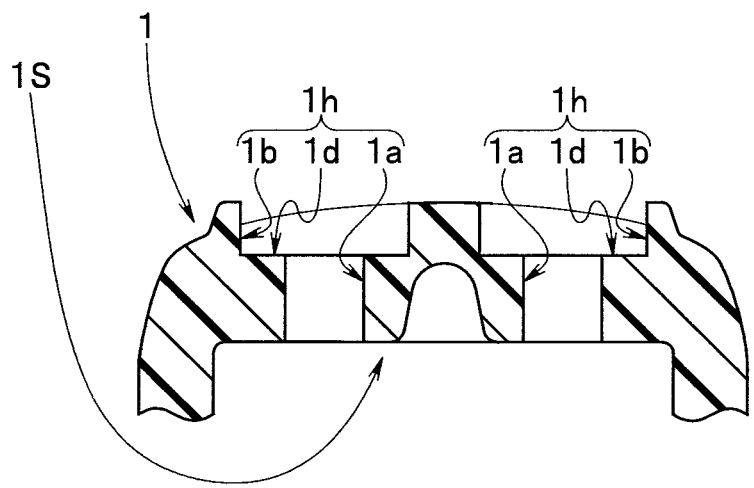
FIG. 1B is a view illustrating the operation section exterior on which the remote switches are disposed.
Figure 1C:
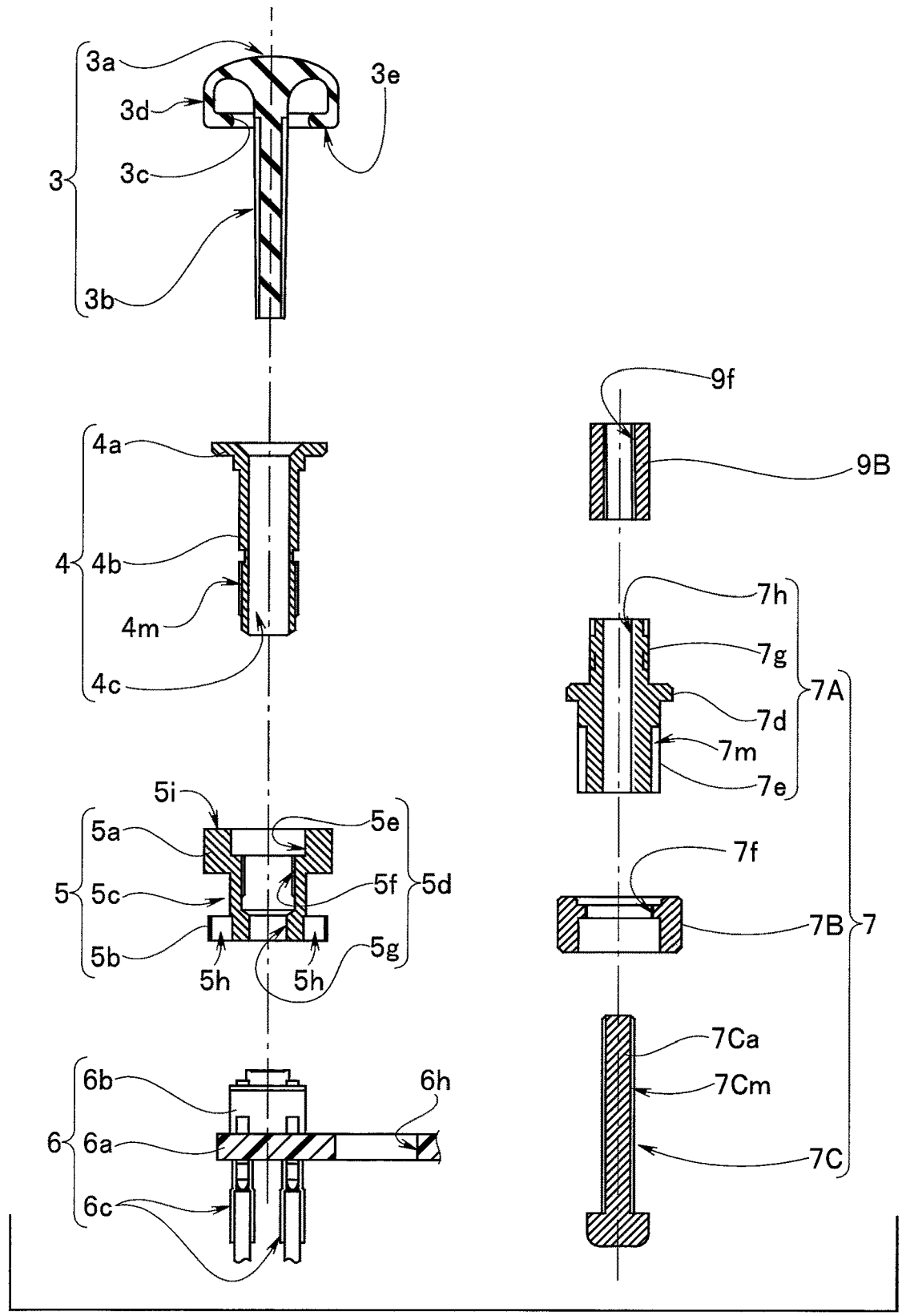
FIG. 1C is a view illustrating the configuration of parts of the remote switch.
Figure 2A:
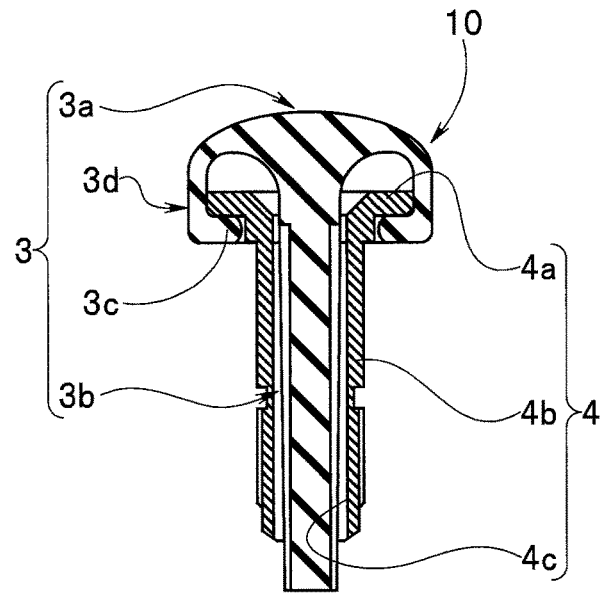
FIG. 2A is a view illustrating a key top set formed of a key top and a guide tube.
Figure 2B:
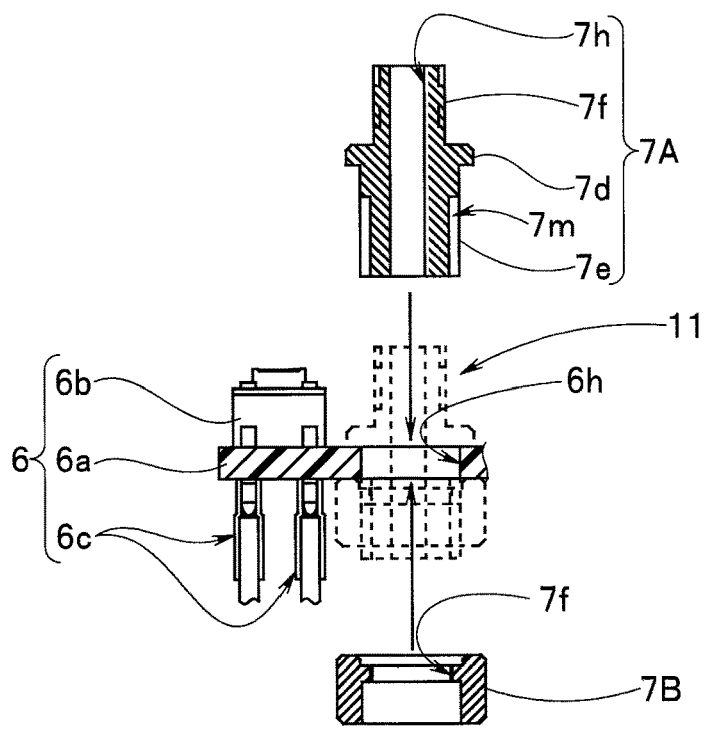
FIG. 2B is a view illustrating a switch set formed of a switch unit, a fixing portion body, and a nut.
Figure 2C:
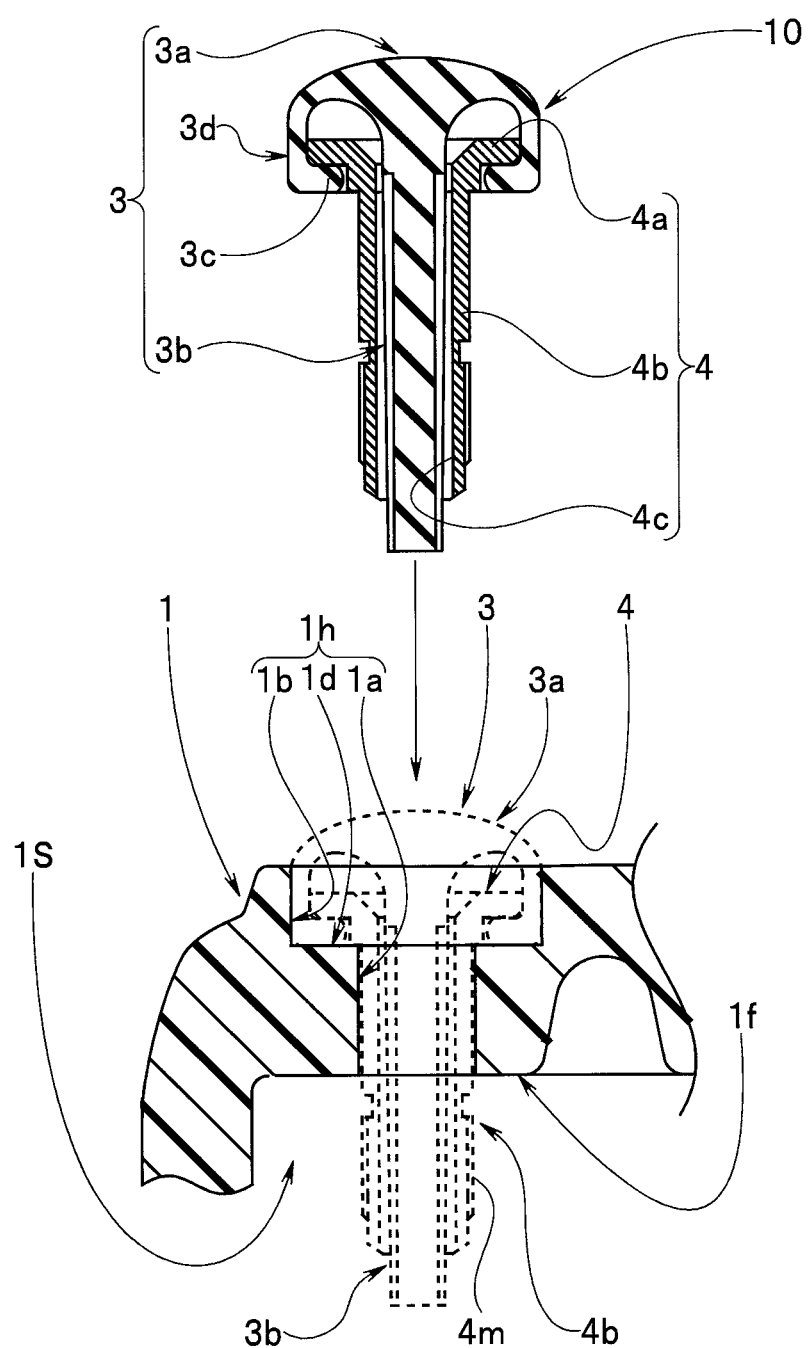
FIG. 2C is a view illustrating mounting of the key top set on the operation section exterior.
Figure 2D:
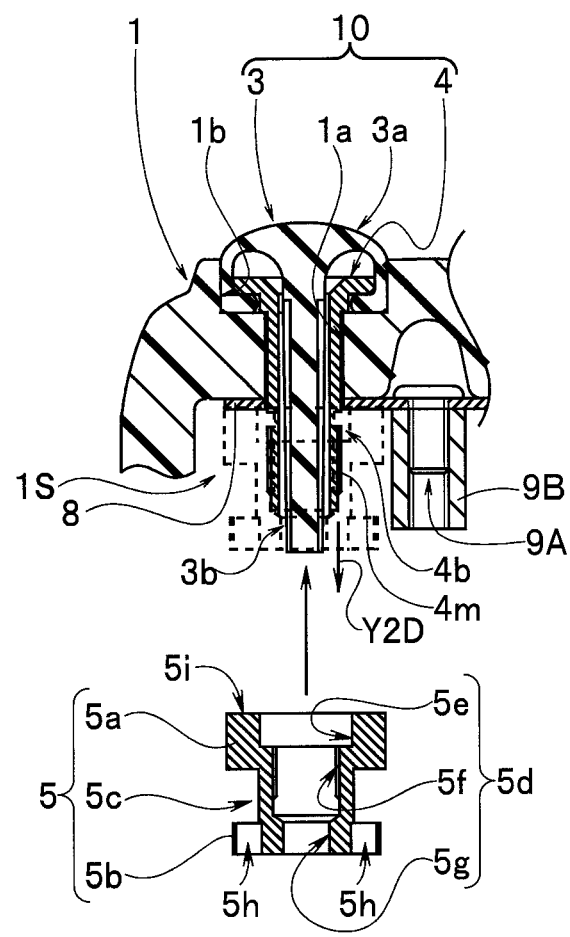
FIG. 2D is a view illustrating fixing of the key top set to the operation section exterior by a guide tube fixing member.
Figure 2E:
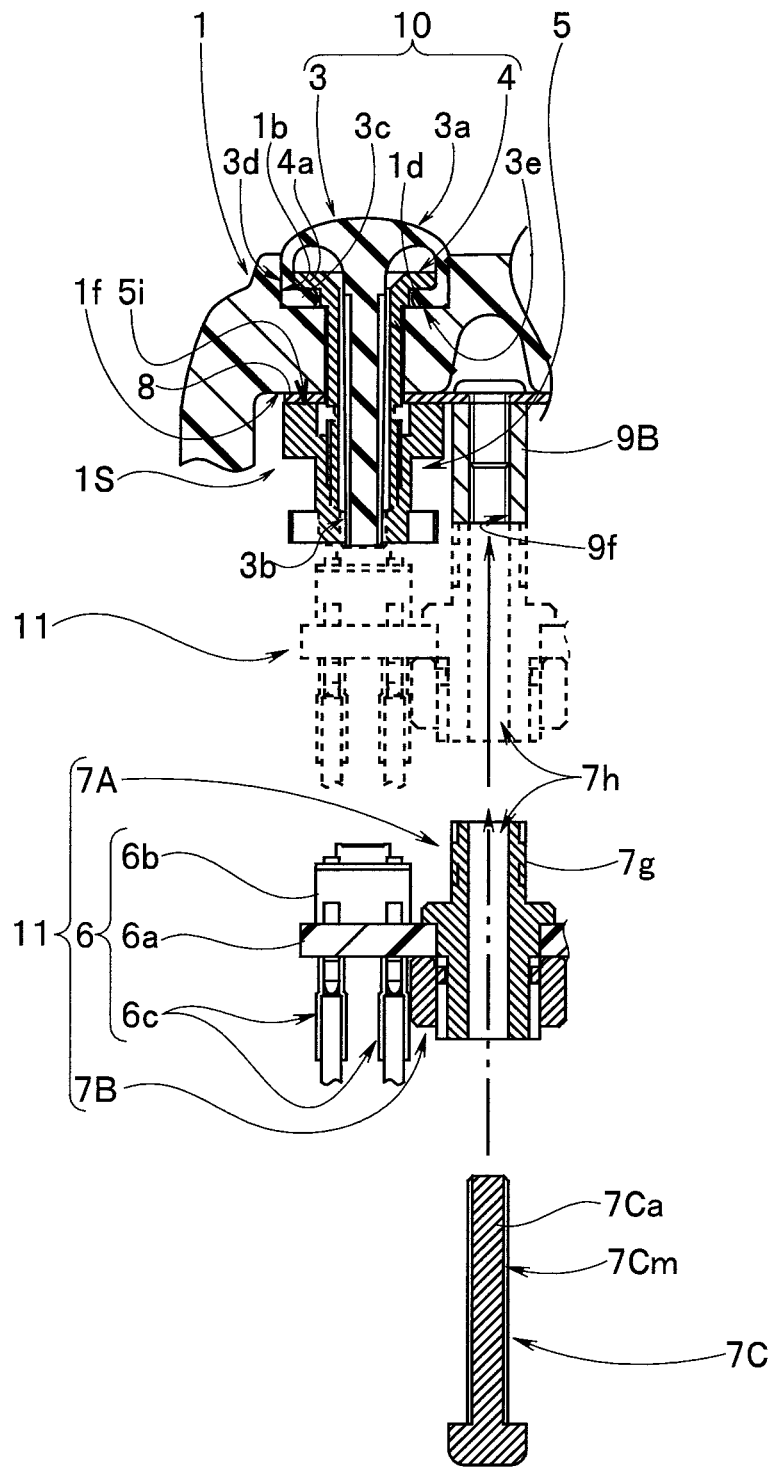
FIG. 2E is a view illustrating mounting of the switch set on the operation section exterior to which the key top set is fixed.
Figure 3:
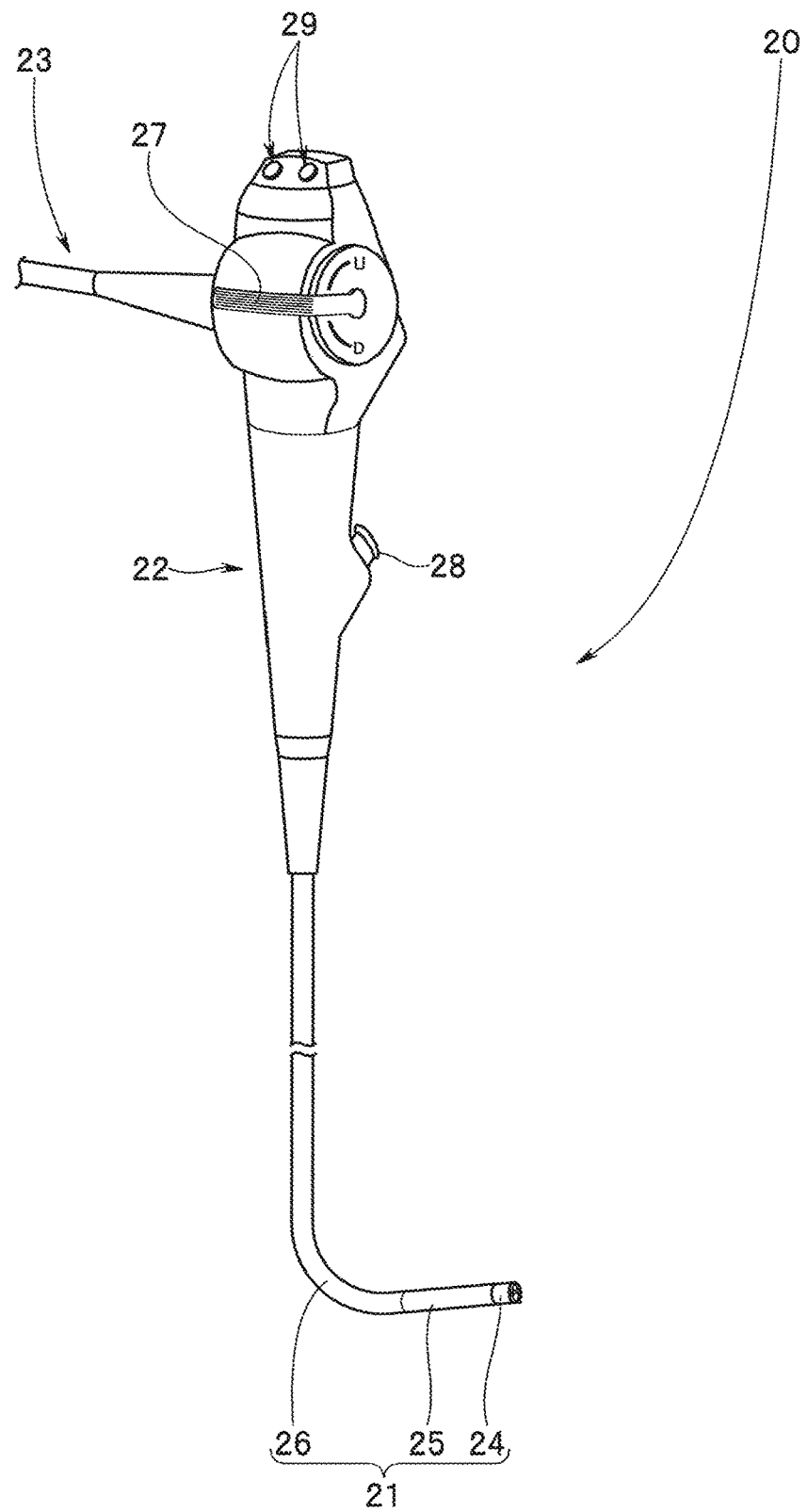
FIG. 3 is a view illustrating one constitutional example of an endoscope where switch units are mounted on an operation section.

An endoscope 20 shown in FIG. 3 mainly includes an endoscope insertion section (hereinafter, abbreviated as an insertion section) 21, an endoscope operation section (hereinafter, abbreviated as an operation section) 22, and a universal cord 23. The insertion section 21 has a narrow diameter, and is formed by connecting a distal end portion 24, a bending portion 25, and a flexible tube portion 26 in this order from a distal end side.

An observation window (not shown in the drawing), an illumination window (not shown in the drawing), a treatment instrument opening (not shown in the drawing) and the like are mounted on a distal end surface of the distal end portion 24. The bending portion 25 is disposed at an intermediate portion of the insertion section 21, and is formed so as to bend in a vertical direction, for example. The flexible tube portion 26 is a tube body having flexibility, and is formed so as to bend passively.

The operation section 22 is mounted on a proximal end side of the flexible tube portion 26. The universal cord 23 extends from a side portion of the operation section 22. An endoscope connector (not shown in the drawing) is mounted on a proximal end portion of the universal cord 23. The endoscope connector is detachably mounted on a light source device or the like which forms an external equipment.

The operation section 22 includes a bending operation device 27, a treatment instrument insertion opening 28, a plurality of remote switches 29, a suction opening (not shown in the drawing) and the like.

The bending operation device 27 is, for example, a lever having an L shape. A proximal end portion of the lever is rotatably and pivotally supported on the operation section 22. The bending operation device 27 is operated when a user performs a bending operation of the bending portion 25. The bending portion 25 is bent in an upward direction or in a downward direction when an upward or downward towing wire is towed or slackened along with a rotating operation of the bending operation device 27.

The above-mentioned bending portion 25 is not limited to the configuration where the bending portion 25 is bent in the vertical direction, but may have the configuration where the bending portion 25 is bent in four directions, that is, the upward direction, the downward direction, the leftward direction, and the rightward direction. In this case, the operation section 22 includes an upward and downward lever and a leftward and rightward lever. The leftward and rightward operation lever is configured to bend the bending portion 25 in the leftward direction or in the rightward direction by towing or slackening the leftward or the rightward towing wire by a rotating operation.

The bending operation device 27 is not limited to the lever having an L shape, but may be a rotary knob which has an approximately circular shape and is rotatably operated, a rod-shaped lever of a joystick type which is tiltably operated or the like.

Various treatment instruments are inserted from the treatment instrument insertion opening 28. The plurality of remote switches 29 are operation switches for performing stopping, recording, or enlarging of an endoscope image displayed on a screen of a display device (not shown in the drawing), switching of an illumination light or the like. The remote switches 29 are mounted on an operation section exterior member 30 of the operation section 22.

The remote switches 29 are described with reference to FIG. 4 to FIG. 8E.

Figure 4:
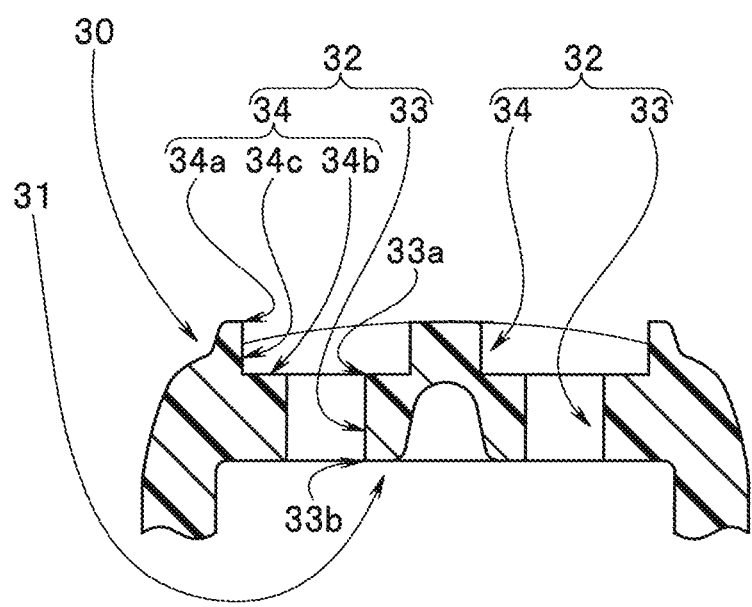
FIG. 4 is a view illustrating an operation section exterior member on which the switch units are mounted.

As shown in FIG. 4, stepped holes 32 which are through holes communicating with the outside of the operation section and an operation section inner space 31 are formed in the operation section exterior member 30. The stepped hole 32 is a hole in which the remote switch 29 is disposed, and has a small diameter hole 33 and a large diameter hole 34.

The large diameter hole 34 has an outside opening 34a. The large diameter hole 34 includes a bottom surface 34b and an inner peripheral surface 34c. One opening 33a of the small diameter hole 33 is formed in the bottom surface 34b. The other opening 33b of the small diameter hole 33 is a space-side opening, and communicates with the operation section inner space 31.

Figure 5:
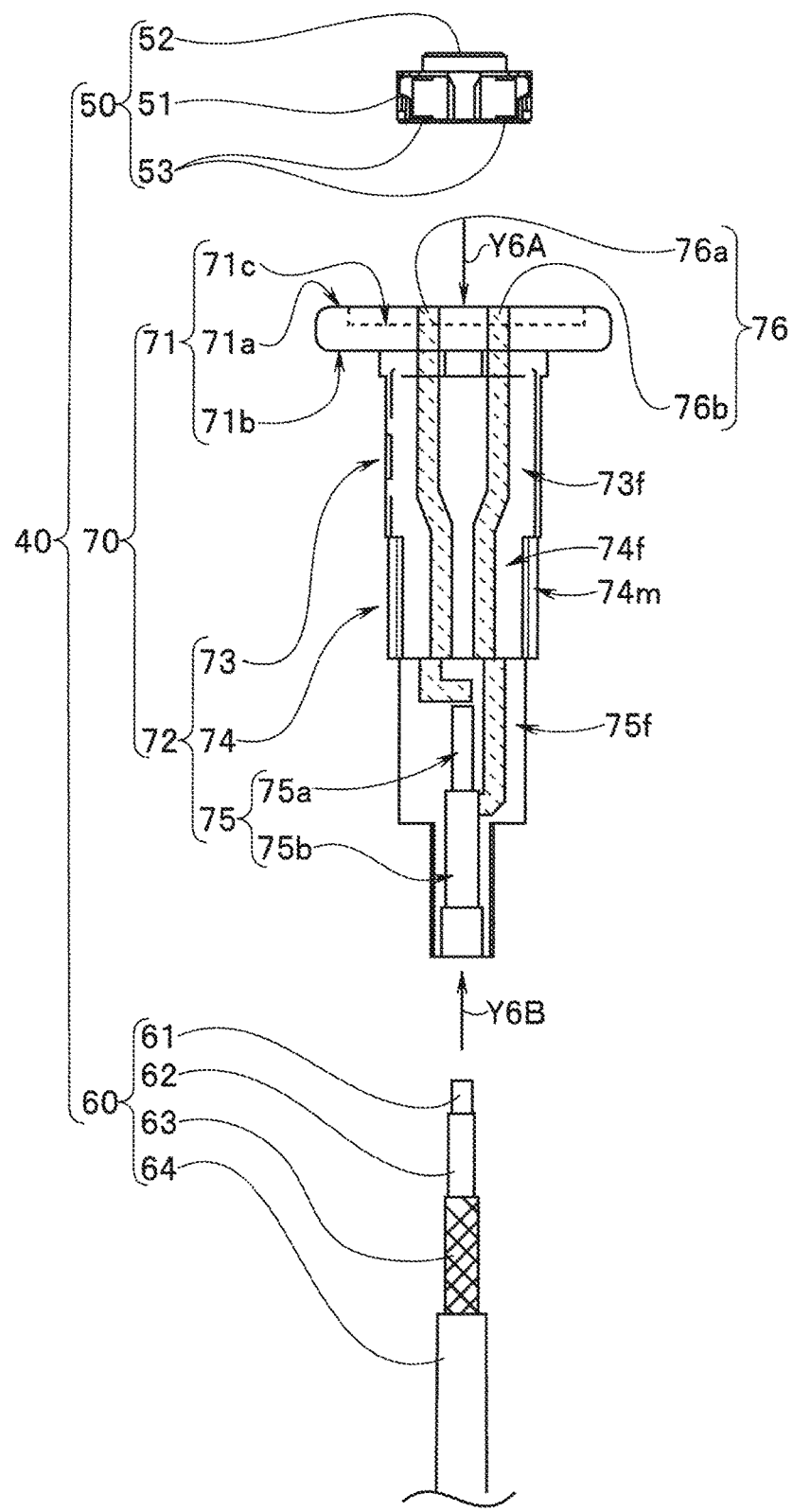
FIG. 5 is a view illustrating the switch unit.

As shown in FIG. 5, the switch unit 40 includes a tactile switch 50, a cable 60, and a formed part 70. The tactile switch 50 is formed of an exterior body 51, an operation portion 52, a plurality of contacts 53 and the like. The tactile switch 50 is, for example, a momentary switch where a contact mechanism is brought into an ON state while obtaining click feeling when the operation portion 52 is pushed.

The cable 60 is, for example, a coaxial cable. The cable 60 includes an inner conductive body 61, an insulating body 62, an outer conductive body 63, and a protective cover 64 in this order from a center axis side. The protective cover 64 forms an outermost layer of the cable 60. The insulating body 62 forms an intermediate layer, and insulates the inner conductive body 61 and the outer conductive body 63 from each other.

The formed part 70 has a first arrangement portion 71 and a second arrangement portion 72. The first arrangement portion 71 has a circular plate shape. The second arrangement portion 72 is disposed on a back surface 71b of the first arrangement portion 71 which is the surface on a side opposite to a front surface 71a of the first arrangement portion 71. The second arrangement portion 72 is provided at a right angle to the back surface 71b.

The front surface 71a of the first arrangement portion 71 forms a switch fixing portion on which the tactile switch 50 is mounted. An end portion side of the second arrangement portion 72 forms a cable fixing portion to which a distal end side of the inner conductive body 61 of the cable 60 and a distal end side of the outer conductive body 63 of the cable 60 are connected.

The second arrangement portion 72 includes a fitting engagement portion 73, a formed part connecting portion (hereinafter, abbreviated as a connecting portion) 74, and a cable fixing portion 75 in this order from a back surface 71b side of the first arrangement portion 71.

The fitting engagement portion 73 is disposed in the small diameter hole 33 of the stepped hole 32. The connecting portion 74 has a male threaded portion 74m with which female threads of a nut described later (indicated by symbol 90 in FIG. 8D) threadedly engages. The cable connecting portion 75 has: a first accommodating portion 75a in which distal end sides of the inner conductive body 61 and the insulating body 62 of the cable 60 are disposed; and a second accommodating portion 75b in which distal end sides of the outer conductive body 63 and the protective cover 64 are disposed.

Symbol 76 indicates a circuit. The circuit 76 is formed of foil portions 76a, 76b. The circuit 76 transmits an operation signal generated by the tactile switch 50 to the cable 60.

Figure 6A:
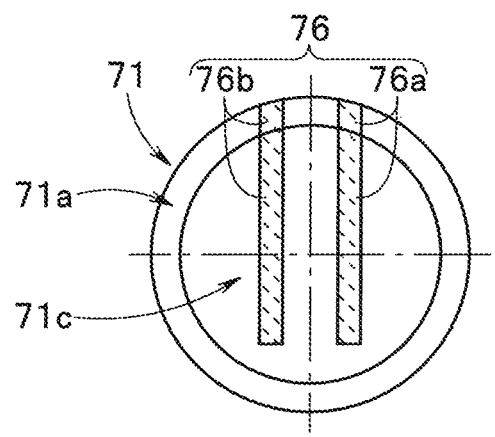
FIG. 6A is a view of a formed part as viewed in a direction indicated by an arrow 6A in FIG. 5.

As shown in FIG. 5 and FIG. 6A, for example, a recessed surface 71c is formed on the front surface 71a of the first arrangement portion 71. The foil portions 76a, 76b which form the circuit 76 are disposed on the recessed surface 71c. In other words, the recessed surface 71c on which the foil portions 76a, 76b are disposed forms a switch fixing portion on which the tactile switch 50 is fixedly mounted. Respective contacts 53 of the tactile switch 50 are connected to the respective foil portions 76a, 76b disposed on the recessed surface 71c in a predetermined state.

The foil portions 76a, 76b of the first arrangement portion 71 are also disposed, in addition to the recessed surface 71c, on the front surface 71a and a raised surface (not shown in the drawing) extending from the recessed surface 71c to the front surface 71a at predetermined positions. The foil portions 76a, 76b on the raised surface connect the foil portions 76a, 76b of the recessed surface 71c and the foil portions 76a, 76b of the front surface 71a to each other.

Figure 6B:
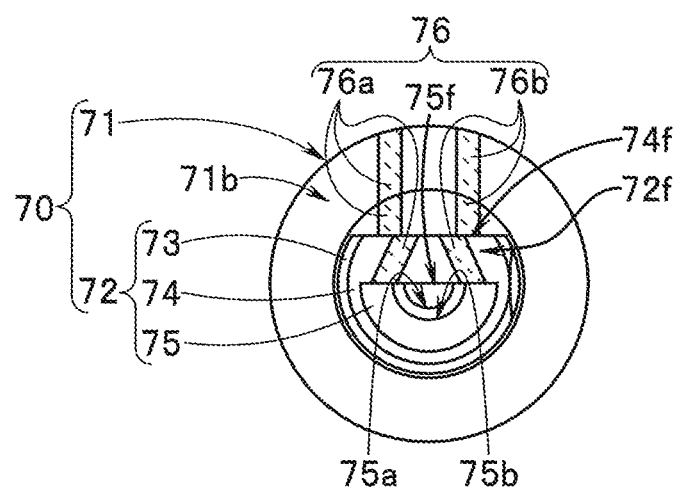
FIG. 6B is a view of the formed part as viewed in a direction indicated by an arrow 6B in FIG. 5.

As shown in FIG. 5 and FIG. 6B, the fitting engagement portion 73, the connecting portion 74, and the cable fixing portion 75 of the second arrangement portion 72 are formed by forming cutout flat surfaces 73f, 74f, 75f on a portion of a circular columnar shape portion. The foil portions 76a, 76b are disposed on the cutout flat surface 73f of the fitting engagement portion 73, the cutout flat surface 74f of the connecting portion 74, the cutout flat surface 75f of the cable connecting portion 75, and a stepped surface 72f extending from the cutout flat surface 74f of the connecting portion 74 to the cutout flat surface 75f of the cable connecting portion 75. The foil portions 76a, 76b disposed on the stepped surface 72f connect the foil portions 76a, 76b disposed on the connecting portion 74 and the foil portions 76a, 76b disposed on the cable connecting portion 75 to each other.

As shown in FIG. 5 and FIG. 6B, the foil portions 76a, 76b are disposed on the back surface 71b of the first arrangement portion 71. Further, on an outer side surface of the first arrangement portion 71, the foil portions 76a, 76b which connect the foil portions 76a, 76b disposed on the front surface 71a and the foil portions 76a, 76b disposed on the back surface 71b to each other are disposed. Further, the above-mentioned male threaded portion 74m is formed on a peripheral surface of the connecting portion 74.

The first accommodating portion 75a and the second accommodating portion 75b are recessed portions having a semicircular cross section. An end part surface with which a distal end surface of the insulating body 62 is brought into contact is formed on the first accommodating portion 75a. A distal end side of the inner conductive body 61 disposed in the first accommodating portion 75a is connected to the first foil portion 76a by a solder, for example. The outer conductive body 63 disposed in the second accommodating portion 75b is connected to the second foil portion 76b by a solder, for example.

Figure 7:
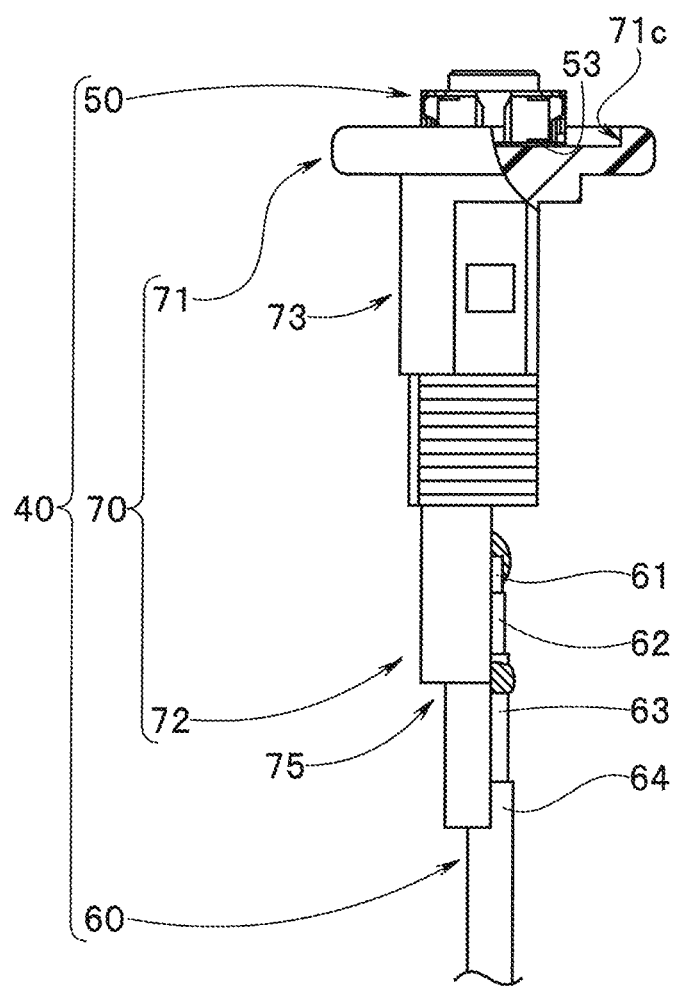
FIG. 7 is a view illustrating the switch unit on which a tactile switch is mounted and to which a cable is connected.

With such a configuration, as shown in FIG. 7, it is possible to form the switch unit 40 where the tactile switch 50 and the cable 60 are fixed to the formed part 70.

In the switch unit 40, the tactile switch 50 is mounted on the switch fixing portion which is the recessed surface 71c formed on the first arrangement portion 71 disposed on a first end portion side of the formed part 70 with respect to the fitting engagement portion 73 positioned at the intermediate portion of the formed part 70. In the switch unit 40, the cable 60 is connected to the cable connecting portion 75 disposed on a second end portion side of the formed part 70 on a side opposite to the recessed surface 71c with the fitting engagement portion 73 which forms the intermediate portion positioned between the recessed surface 71c and the cable connecting portion 75 in a predetermined state, and the cable 60 extends toward the outside of the formed part 70 from a position immediately below the operation portion 52.

In the switch unit 40 having such a configuration, an operation signal generated by operating the operation portion 52 of the tactile switch 50 mounted on the switch fixing portion on a first end portion side is transmitted to the cable 60 connected to the cable fixing portion 75 on the second end portion side via the circuit 76, and is transmitted to an external equipment via the cable 60.

Mounting of the remote switch 29 on the operation section exterior member 30 is described below.

An operator prepares the operation section exterior member 30, the switch unit 40, the key top 80, and the formed part fixing member 90.

Figure 8A:
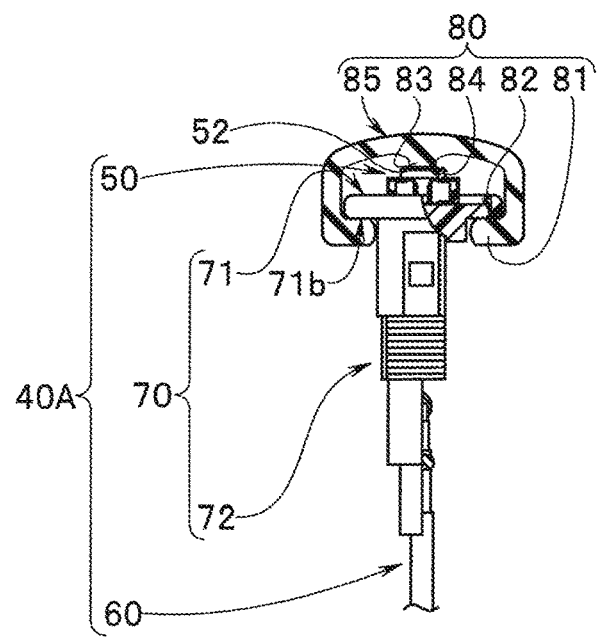
FIG. 8A is a view illustrating a state where a key top is disposed on the switch unit.

In this embodiment, one remote switch 29 is mounted on each stepped hole 32 formed in the operation section exterior member 30. As shown in FIG. 8A, in this embodiment, the key top 80 which is an elastic rubber member and formed in a predetermined shape is disposed in the first arrangement portion 71 of the formed part 70 in advance thus forming a key top equipped switch unit 40A.

Accordingly, the operator prepares, in mounting the remote switch 29, the operation section exterior member 30, the key top equipped switch unit 40A, and the formed part fixing member 90.

The key top 80 has an inner flange portion 81. One surface 82 of the inner flange portion 81 is disposed on a back surface 71b of the first arrangement portion 71. In such an arrangement state, an end surface 84 of the switch pressing convex portion 83 of the key top 80 is disposed in a facing manner with the operation portion 52 of the tactile switch 50 in a predetermined state.

Figure 8B:
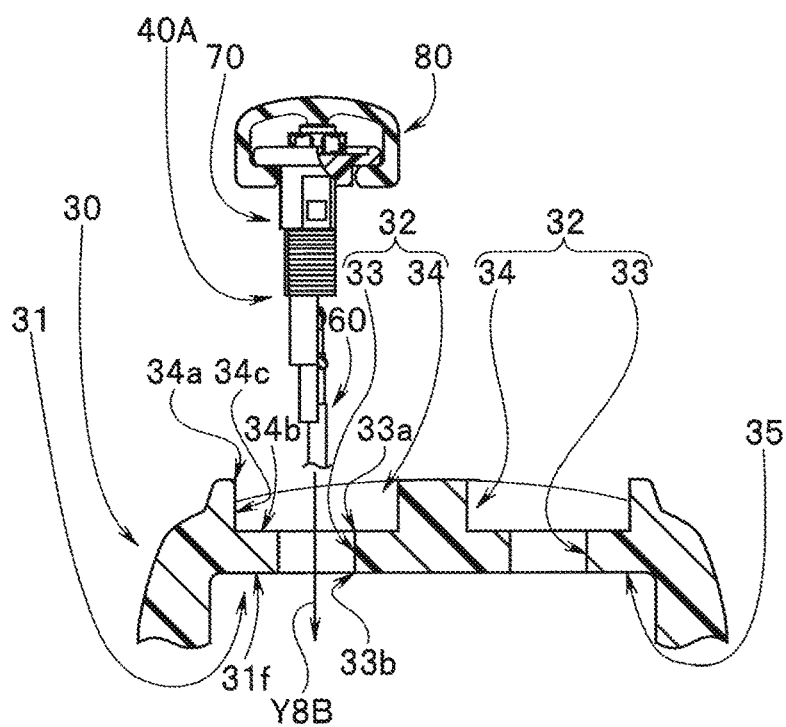
FIG. 8B is a view illustrating a state where the switch unit on which the key top is mounted is disposed on the operation section exterior member.

First, as shown in FIG. 8B, the operator inserts the second arrangement portion 72 including the cable 60 fixed to the formed part 70 which forms the key top equipped switch unit 40A and extends into the small diameter hole 33 of the stepped hole 32 formed in the operation section exterior member 30 as indicated by an arrow Y8B.

Figure 8C:
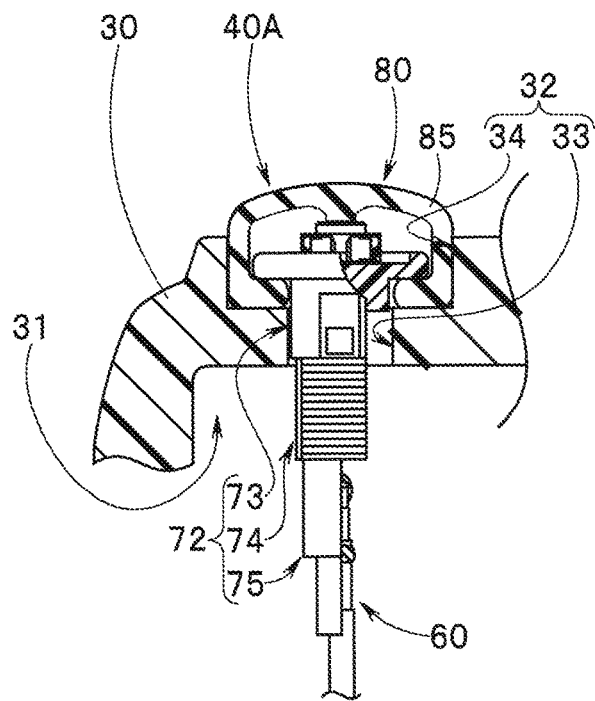
FIG. 8C is a view illustrating a state where a first flat plate portion on which the key top and the tactile switch mounted on the switch unit are disposed is placed in a large diameter hole of a stepped hole.

Then, as shown in FIG. 8C, the operator pulls out the cable fixing portion 75 and the connecting portion 74 of the second arrangement portion 72 from the small diameter hole 33 and arranges the cable fixing portion 75 and the connecting portion 74 in the operation section inner space 31. The operator arranges the fitting engagement portion 73 in the small diameter hole 33, and arranges the finger touch portion 85 of the key top 80 in the large diameter hole 34.

Figure 8D:
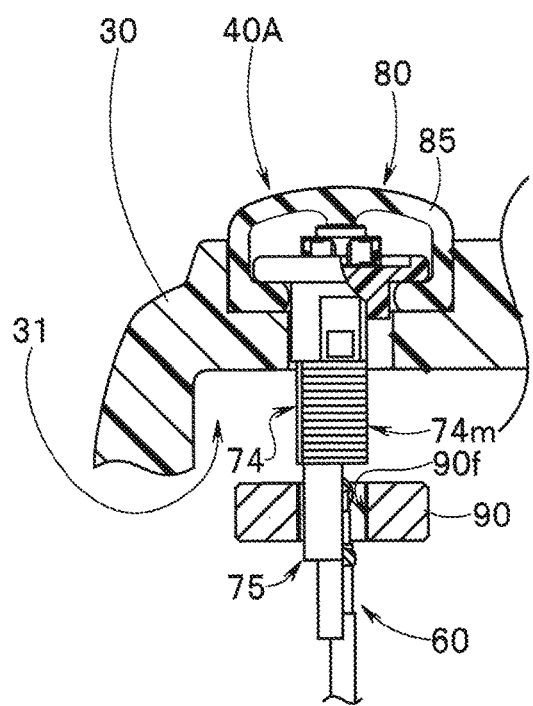
FIG. 8D is a view illustrating a state where a nut is mounted on a connecting portion of a second flat plate portion which protrudes into an operation section inner space.

Next, as shown in FIG. 8D, the operator mounts a nut which forms the formed part fixing member 90 (hereinafter, the formed part fixing member being referred to as the nut 90) on the connecting portion 74 which protrudes into the operation section inner space 31. In other words, female threads 90f of the nut 90 threadedly engage with the male threaded portion 74m of the connecting portion 74.

Figure 8E:
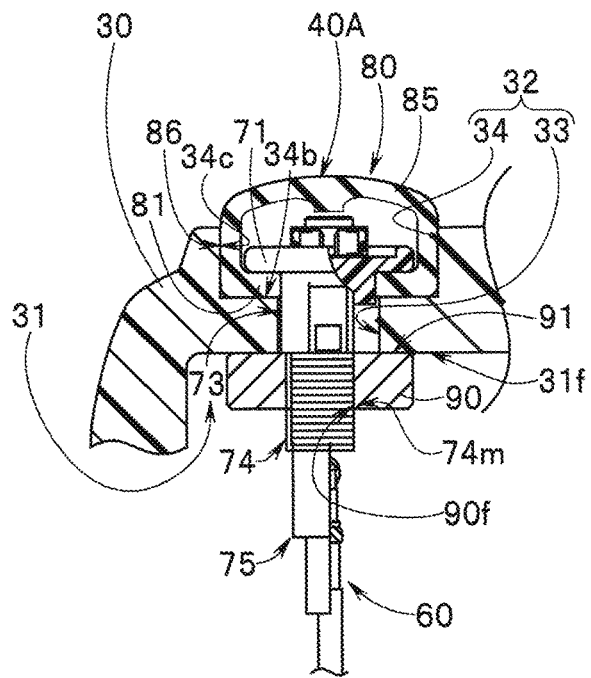
FIG. 8E is a view illustrating a state where the switch unit on which the key top is mounted is fixedly mounted on the operation section exterior member by making the nut threadedly engage with the connecting portion.

As a result, as shown in FIG. 8E, an end surface 91 of the nut 90 is brought into contact with a space flat surface 31f of the operation section inner space 31, the fitting engagement portion 73 is further moved into the operation section inner space 31, and the fitting engagement portion 73 of the formed part 70 is fixedly mounted on the operation section exterior member 30 in a state where the fitting engagement portion 73 of the formed part 70 is disposed in the small diameter hole 33.

At this stage of operation, the first arrangement portion 71 presses the inner flange portion 81 so that the inner flange portion 81 is elastically deformed. As a result, a lower end surface of the key top 80 is brought into close contact with the bottom surface 34b, and the outer peripheral surface 86 of the key top 80 is brought into close contact with the inner peripheral surface 34c of the large diameter hole 34 and hence, the key top 80 is fixed to the operation section exterior member 30.

With such operations, the remote switch 29 is mounted on and fixed to the operation section exterior member 30.

In this manner, the switch unit 40 is formed as followed. The formed part 70 is formed of the first arrangement portion 71 which includes the switch fixing portion and the second arrangement portion 72 which includes the cable fixing portion, and the circuit 76 which connects the switch fixing portion and the cable fixing portion to each other is disposed on the first arrangement portion 71 and the second arrangement portion 72. Further, the tactile switch 50 is mounted on the switch fixing portion in advance, and the cable 60 is connected to the switch fixing portion in advance.

As a result, it is possible to realize the switch unit having the configuration which can be manufactured at a low cost by largely reducing the number of parts which form the remote switch 29.

Further, the connecting portion 74 having the male threaded portion 74m is formed on the second arrangement portion 72, and the female threaded portion of the nut 90 is threaddedly engaged with the male threaded portion 74m of the connecting portion 74. Accordingly, the formed part 70 is integrally fixed to the operation section exterior member 30 in a state where the fitting engagement portion 73 is fitted and disposed in the small diameter hole 33.

As a result, the key top 80 and the switch unit 40 can be disposed in the stepped hole 32 at a predetermined position and hence, the key top 80 and the switch unit 40 can be easily mounted on and fixed to the operation section exterior member 30.

Accordingly, it is possible to provide an endoscope which can be manufactured at a low cost by easily mounting the inexpensive switch unit 40 on the operation section exterior member 30.

Further, by arranging the first arrangement portion 71 on which the switch unit 40 is mounted in the large diameter hole 34 of the stepped hole 32, the connecting portion 74 and the cable fixing portion 75 can be disposed in the operation section inner space 31 immediately below the operation portion 52 and hence, the operation section inner space 31 can be effectively utilized.

Figure 9:
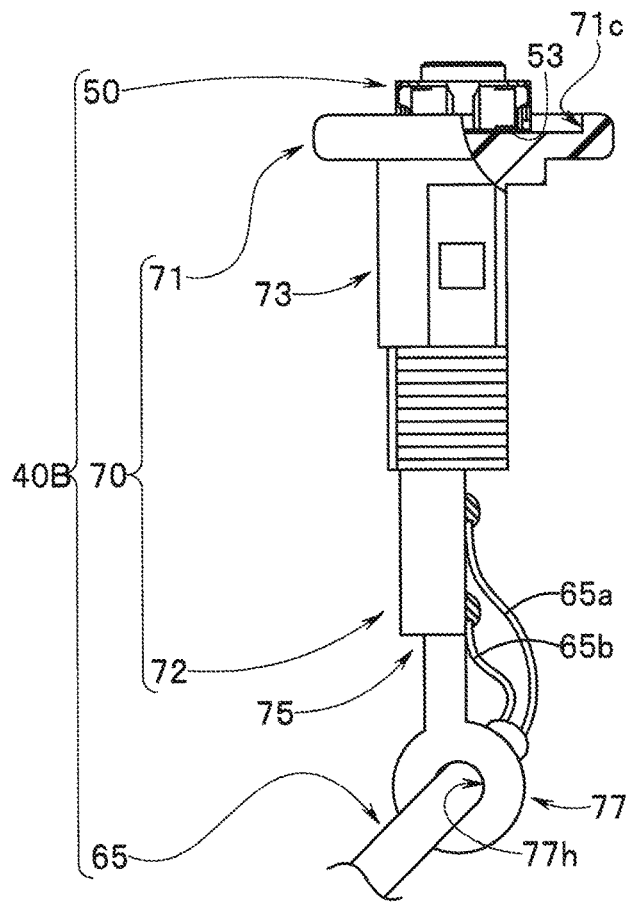
FIG. 9 is a view showing another constitutional example of the switch unit.

In the above-mentioned embodiment, the cable 60 is formed of a coaxial cable. However, the cable is not limited to a coaxial cable. The cable may be a signal cable 65 through which two signal lines pass. In this case, as shown in FIG. 9, two signal lines 65a, 65b of the signal cable 65 are connected to the foil portions 76a, 76b by a solder as described previously. Symbol 77 indicates a signal cable insertion portion, and has a cable hole 77h. The signal cable 65 passes through the cable hole 77h.

In the above-mentioned embodiment, the foil portions 76a, 76b disposed on the recessed surface 71c and the foil portions 76a, 76b disposed on the cutout flat surface 73f are connected to each other by the foil portions 76a, 76b formed on the front surface 71a, the outer side surface of the first arrangement portion 71, and the back surface 71b. However, the configuration may be adopted where a hole which passes through the first arrangement portion 71 between the front surface 71a and the back surface 71b is formed in the first arrangement portion 71 at a predetermined position, and foil portions which connect the foil portions 76a, 76b disposed on the recessed surface 71c and the foil portions 76a, 76b disposed in the cutout flat surface 73f are formed on one surface of the hole.

The present invention is not limited only to the above-mentioned embodiment, and various modifications can be carried out without departing from the gist of the present invention.

According to the present invention, it is possible to realize a switch unit which can be manufactured at a low cost while realizing downsizing due to reduction of the number of parts and exhibits excellent mountability, and an endoscope provided with such a switch unit.

What is claimed is:

1. A switch unit mounted on an exterior member, the switch unit comprising:
    a tactile switch;
    a cable configured to transmit a signal of the tactile switch; and
    a single molded body disposed on the exterior member at a predetermined position, wherein the single molded body comprises:
        a switch fixing portion formed on a first end portion of the single molded body and on which the tactile switch is mounted;
        a cable fixing portion formed on a second end portion of the single molded body, the second end portion being opposite to the first end portion, the cable being connected to the cable fixing portion; and
        a circuit formed on the single molded body, the circuit electrically connecting the switch fixing portion and the cable fixing portion.

2. The switch unit according to claim 1, further comprising a key top disposed on the single molded body to cover the tactile switch, the key top being fixed to the exterior member by the single molded body.

3. The switch unit according to claim 2, wherein the single molded body comprises:
    a first arrangement portion on which the switch fixing portion is formed; and
    a second arrangement portion on which the cable fixing portion is formed, and
    the second arrangement portion is disposed orthogonal to an opposite side surface of the switch fixing portion of the first arrangement portion.

4. The switch unit according to claim 3, wherein the cable fixed to the cable fixing portion is pulled out to an outside of the single molded body from a position immediately below an operation portion of the tactile switch fixed to the switch fixing portion.

5. The switch unit according to claim 1, wherein the single molded body includes a first arrangement portion on which the switch fixing portion is formed, and a second arrangement portion on which the cable fixing portion is formed, and
    the circuit is a foil portion formed on both of a surface of the first arrangement portion and a surface of the second arrangement portion.

6. The switch unit according to claim 1, wherein the single molded body includes a first arrangement portion on which the switch fixing portion is formed, and a second arrangement portion on which the cable fixing portion is formed, and
    the exterior member has a stepped hole formed of a large diameter portion and a small diameter portion having a diameter smaller than a diameter of the large diameter portion, and the first arrangement portion is disposed in the large diameter portion.

7. The switch unit according to claim 6, wherein the tactile switch is configured to be pressed downward in a direction from the large diameter portion to the small diameter portion.

8. The switch unit according to claim 1, wherein the single molded body has an intermediate portion formed so as to arrange the single molded body on the exterior member at a predetermined position, and
    the second end portion is disposed on a side opposite to the first end portion with the intermediate portion positioned between the first end portion and the second end portion.

9. The switch unit according to claim 1, wherein the first end portion is disposed outside the exterior member.

10. An endoscope comprising:
    an endoscope operation section having the exterior member; and
    the switch unit according to claim 1, the switch unit being mounted on the endoscope operation section.

11. The switch unit according to claim 1, wherein the circuit is formed on a surface of the single molded body.

12. The switch unit according to claim 1, wherein the first end portion being opposite to the second end portion in a direction of a longitudinal axis of the single molded body.

13. An endoscope comprising:
- an insertion section;
- an operation section mounted on a proximal end side of the insertion section;
- a universal cord extending sideward from the operation section;
- a tactile switch mounted on the operation section;
- a cable disposed in the universal cord and is configured to transmit a signal of the tactile switch;
- a single molded body which includes an intermediate portion disposed on the operation section at a predetermined position, wherein the single molded body comprising:
  - a switch fixing portion formed on a first end portion of the single molded body with respect to the intermediate portion, and on which the tactile switch is mounted,
  - a cable fixing portion formed on a second end portion of the single molded body, the second end portion being opposite to the first end portion with the intermediate portion positioned between the first end portion and the second end portion, the cable being connected to the cable fixing portion; and
  - a circuit formed on the single molded body, the circuit electrically connecting the switch fixing portion and the cable fixing portion to each other.

\* \* \* \* \*